(12) United States Patent
Goldblatt (10) Patent No.: US 10,281,383 B2
(45) Date of Patent: May 7, 2019

(54) SYSTEM AND METHODS OF DETERMINING LIQUID PHASE TURBIDITY OF MULTIPHASE WASTEWATER

(71) Applicant: Solenis Technologies, L.P., Schaffhausen (CH)

(72) Inventor: Mikel E. Goldblatt, Jenkintown, PA (US)

(73) Assignee: SOLENIS TECHNOLOGIES, L.P., Schaffhausen (CH)

(*) Notice: Subject to any disclaimer, the term of this patent is extended or adjusted under 35 U.S.C. 154(b) by 58 days.

(21) Appl. No.: 14/075,613

(22) Filed: Nov. 8, 2013

(65) Prior Publication Data

US 2014/0131259 A1 May 15, 2014

Related U.S. Application Data

(60) Provisional application No. 61/726,637, filed on Nov. 15, 2012.

(51) Int. Cl.
*G01N 15/06* (2006.01)
*C02F 1/00* (2006.01)
(Continued)

(52) U.S. Cl.
CPC .......... *G01N 15/06* (2013.01); *A47L 15/4297* (2013.01); *C02F 1/5209* (2013.01);
(Continued)

(58) Field of Classification Search
CPC .......... C02F 1/00; C02F 1/008; C02F 1/5209; C02F 1/24; C02F 1/5245; C02F 1/56;
(Continued)

(56) References Cited

U.S. PATENT DOCUMENTS 6,408,227 B1 * 6/2002 Singhvi et al. ............... 700/266
6,750,063 B1 6/2004 Kawamura
(Continued)

FOREIGN PATENT DOCUMENTS

CN 101263379 B 9/2008
CN 101999072 A 3/2011
(Continued)

OTHER PUBLICATIONS

International Search Report and Written Opinion of Application No. PCT/US13/69844, dated Mar. 10, 2014, 13 pages.
(Continued)

*Primary Examiner* — Heidi R Kelley
*Assistant Examiner* — Akash K Varma
(74) *Attorney, Agent, or Firm* — Lorenz & Kopf, LLP (57) ABSTRACT

Systems and methods for determining liquid phase turbidity of multiphase wastewater. A turbidity sensor is provided with multiphase wastewater, such as by placement of the sensor in a reaction chamber, and generates a signal in response to a detected turbidity of the wastewater. The generated signal is sampled to produce a plurality of signal samples. The samples are compared to a threshold, and a turbidity of the wastewater is determined based on samples falling within the threshold. The threshold may be determined based on a statistical analysis of the plurality of samples, or may be set to a predetermined value. The wastewater may be provided by placing the turbidity sensor in a flocculation chamber, and a control signal generated based on the determined turbidity of the wastewater. This control signal may be used to adjust the amount of a chemical, such as a coagulant, introduced into the wastewater.

17 Claims, 7 Drawing Sheets

(51) Int. Cl.

| | | |
|---|---|---|
| *C02F 1/52* | (2006.01) | |
| *G01N 21/53* | (2006.01) | |
| *A47L 15/42* | (2006.01) | |
| *G01N 21/51* | (2006.01) | |
| *C02F 1/24* | (2006.01) | |
| *C02F 1/56* | (2006.01) | |
| *C02F 1/66* | (2006.01) | |

(52) U.S. Cl.
 CPC ............ *G01N 21/51* (2013.01); *G01N 21/532* (2013.01); *G01N 21/534* (2013.01); *C02F 1/24* (2013.01); *C02F 1/5245* (2013.01); *C02F 1/56* (2013.01); *C02F 1/66* (2013.01); *C02F 2209/001* (2013.01); *C02F 2209/006* (2013.01); *C02F 2209/11* (2013.01); *G01N 2015/0693* (2013.01)

(58) Field of Classification Search
 CPC ............... C02F 1/66; C02F 2209/001; C02F 2209/006; C02F 2209/11; G01N 15/06; G01N 21/51; G01N 21/532; G01N 21/534; G01N 2015/0693; A47L 15/4297
 USPC ................. 210/745, 96.1; 356/337
 See application file for complete search history.

(56) References Cited

U.S. PATENT DOCUMENTS

| | | |
|---|---|---|
| 6,811,706 B1 | 11/2004 | Wahlberg |
| 2004/0265177 A1 | 12/2004 | Nicoli et al. |
| 2005/0121394 A1 | 6/2005 | Wu et al. |
| 2007/0008540 A1 | 1/2007 | Vanhove et al. |
| 2007/0134804 A1 | 6/2007 | Fisher et al. |
| 2008/0047903 A1 | 2/2008 | Morse |
| 2011/0043807 A1* | 2/2011 | Andelic et al. ............... 356/441 |
| 2011/0060533 A1 | 3/2011 | Jorden et al. |

FOREIGN PATENT DOCUMENTS

| | | |
|---|---|---|
| SU | 1043495 A1 | 9/1983 |
| TW | 201140267 | 11/2011 |

OTHER PUBLICATIONS

Search Report for Patent Application ROC TW No. 102141751, dated Mar. 14, 2017.
State Intellectual Property Office of the People's Republic of China, First Search, Patent Application No. 201380059518.6 dated Jun. 23, 2016.
State Intellectual Property Office of the People's Republic of China, Office Action in Chinese Patent Application No. 201380059518.6 dated Jul. 4, 2016.
State Intellectual Property Office of the People's Republic of China, Office Action in Chinese Patent Application No. 201380059518.6 dated Jun. 21, 2017.
Federal Service for Intellectual Property, Office Action in Russian Patent Application No. 2015122396 dated Aug. 31, 2017.

* cited by examiner

SYSTEM AND METHODS OF DETERMINING LIQUID PHASE TURBIDITY OF MULTIPHASE WASTEWATER

CROSS-REFERENCE TO RELATED APPLICATIONS

This application claims the benefit of and priority to co-pending U.S. Provisional Application Ser. No. 61/726,637, filed Nov. 15, 2012 and entitled "SYSTEM AND METHODS OF DETERMINING LIQUID PHASE TURBIDITY OF MULTIPHASE WASTEWATER", the disclosure of which is incorporated by reference herein in its entirety.

TECHNICAL FIELD

The present invention relates generally to wastewater treatment and, more particularly, to a system and methods for wastewater treatment that determines liquid phase turbidity of multiphase wastewater and adjusts the quantity of chemicals added to the wastewater based thereon.

BACKGROUND

Chemically treating wastewater to reduce contaminants is used in many industrial processes to allow reuse of wastewater, and to ensure that wastewater discharge meets required environmental quality standards. The type of treatment employed depends on the wastewater source, the type of contaminants in the wastewater, and the intended use of the treated water. Wastewater often contains suspended solids comprising particles finer than about 0.1 µm, which are not only difficult to filter out, but tend to remain in suspension indefinitely due to the repelling effects of electrostatic charges between the particles. To reduce the amount of fine particle contamination, or turbidity of the water, treatment systems typically introduce coagulating and/or flocculating agents into the wastewater. The coagulating agent neutralizes the electrostatic charges on the particles, which allows the particles to come into contact with each other and form larger particles. The flocculant may accelerate the agglomeration process by causing colloids and other suspended particles in the wastewater to aggregate, thereby forming large particles commonly referred to as floc particles or floc. The floc may then be removed from the treated water by, for example, sedimentation and/or floatation.

Coagulating and flocculating agents are typically added to wastewater in a mixing or reaction tank. Additional chemicals, such as acids or bases that are added to adjust the pH of the water to improve the effectiveness of the coagulant, or chemicals that react with and neutralize other contaminants, may also be added at this stage. The amount of the agents that must be added depends on the level of contamination and the volume of water being treated. For example, if too little of the coagulating agent is added, the turbidity of the wastewater may not be sufficiently reduced. On the other hand, adding excessive amounts of chemicals to the wastewater results in wasted chemicals, and can also result in the agents themselves becoming unwanted contaminants in the treated effluent.

To determine if sufficient chemical treatment agents are being added to the wastewater, samples of the treated wastewater may be taken and analyzed by measuring turbidity, pH, and/or chemical content. Typically, the wastewater samples must be allowed to settle before measuring turbidity so that the floc particles do not interfere with the measurement. For this reason, samples are typically taken after the sedimentation and/or floatation stages of treatment. However, water samples obtained at this stage of treatment may reflect chemical levels from hours earlier. Thus, by the time an increase in turbidity or the chemical content of the wastewater is detected, the amount of treatment agents present in the reaction tank may have drifted significantly away from their optimum level. In addition, because the contamination level of the inflowing wastewater may change over time, the measurements of samples that reflect wastewater introduced into the reaction tank hours earlier may not provide an accurate indication of how much treatment agent needs to be added to the reaction tank at the present time. The sedimentation or flotation effluent sample measurement may thereby provide an inaccurate indication of how much of a treatment chemical needs to be added to the incoming wastewater.

Consequently, there is a need for improved systems and methods for determining the turbidity of wastewater, as well as the optimum amount of chemicals to add to wastewater in a wastewater treatment system.

SUMMARY

In one embodiment, a method of determining the turbidity of wastewater is provided. The method includes receiving a signal indicative of an amount of light scattered by the wastewater and sampling the signal to produce a plurality of signal sample values. These sample values are compared to a threshold, and the sample values falling inside the threshold identified. The method further includes determining the turbidity of the wastewater based on the sample values falling inside the threshold.

In another embodiment, an apparatus for treating wastewater is provided. The apparatus includes a processor and a memory that contains program code. The program code is configured so that when the code is executed by the processor, the code causes the apparatus to receive a signal indicative of an amount of light scattered by the wastewater and sample the signal to produce a plurality of signal sample values. The code is further configured to cause the apparatus to compare the sample values to a threshold, identify the sample values falling inside the threshold, and determine the turbidity of the wastewater based on the sample values falling inside the threshold.

In some embodiments of the invention, the signal indicative of the amount of light scattered by the wastewater may be generated by detecting an amount of light scattered from a beam of light by the wastewater, in which case the signal may have a higher value (i.e., more light would be detected) for turbid water than for clear water. In other embodiments, this signal may be generated by detecting an amount of light transmitted through the wastewater, in which case the signal may have a lower value (i.e., less light would be detected) for turbid water than for clear water.

In some embodiments of the invention, the threshold may be determined based on a probability density distribution of the plurality of the sample values. The probability density distribution produced by sample values from multiphase wastewater may have two pronounced peaks. One of these peaks may result from sample values produced from light scattered by liquid phase or bulk water without additional scattering or reflections from floc. That is, one peak may be produced from scattering by the wastewater when floc particles have not drifted into the path of the beam of light. The other peak may be produced from scattering by the wastewater when floc particles are present in the path of the beam of light, which may increase the amount of scattering. The threshold may be set to a value between these two peaks to classify sample values as being indicative of wastewater turbidity or as being indicative of floc scattering. Because thresholds determined this way are based on sensor data, the threshold may be adjusted or moved in response to the condition of the wastewater so that sample values are optimally classified.

In some embodiments of the invention, sample values that are classified as being produced by bulk water in the absence of floc may be used to produce a signal or value indicative of the turbidity of the wastewater. This value may then be used to provide feedback to a controller for controlling an operation associated with wastewater treatment, such as an amount of a treatment chemical dispensed into a reaction tank.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the principles of the invention.

DETAILED DESCRIPTION

Embodiments of the invention are directed to systems and methods for measuring turbidity of wastewater in a treatment tank of a wastewater treatment system prior to flotation or sedimentation. This may be accomplished by distinguishing light scattering caused by liquid phase or "bulk water" from light scattering that includes scattering caused by solid phase particles or floc. These measurements, in turn, may be used to control the amount of chemicals dispensed into the wastewater. The wastewater in the treatment tank may contain floc particles that generate erroneous turbidity sensor readings. The system includes a controller configured to sample an output signal of a turbidity sensor, and to process the output signal samples to identify samples that are associated with scattering by bulk water in the treatment tank. The controller may then determine the turbidity of the wastewater based on the identified samples. The controller may also be configured to adjust the amount of one or more chemicals dispensed into or upstream or downstream of the treatment tank based on the determined turbidity.

Figure 1:
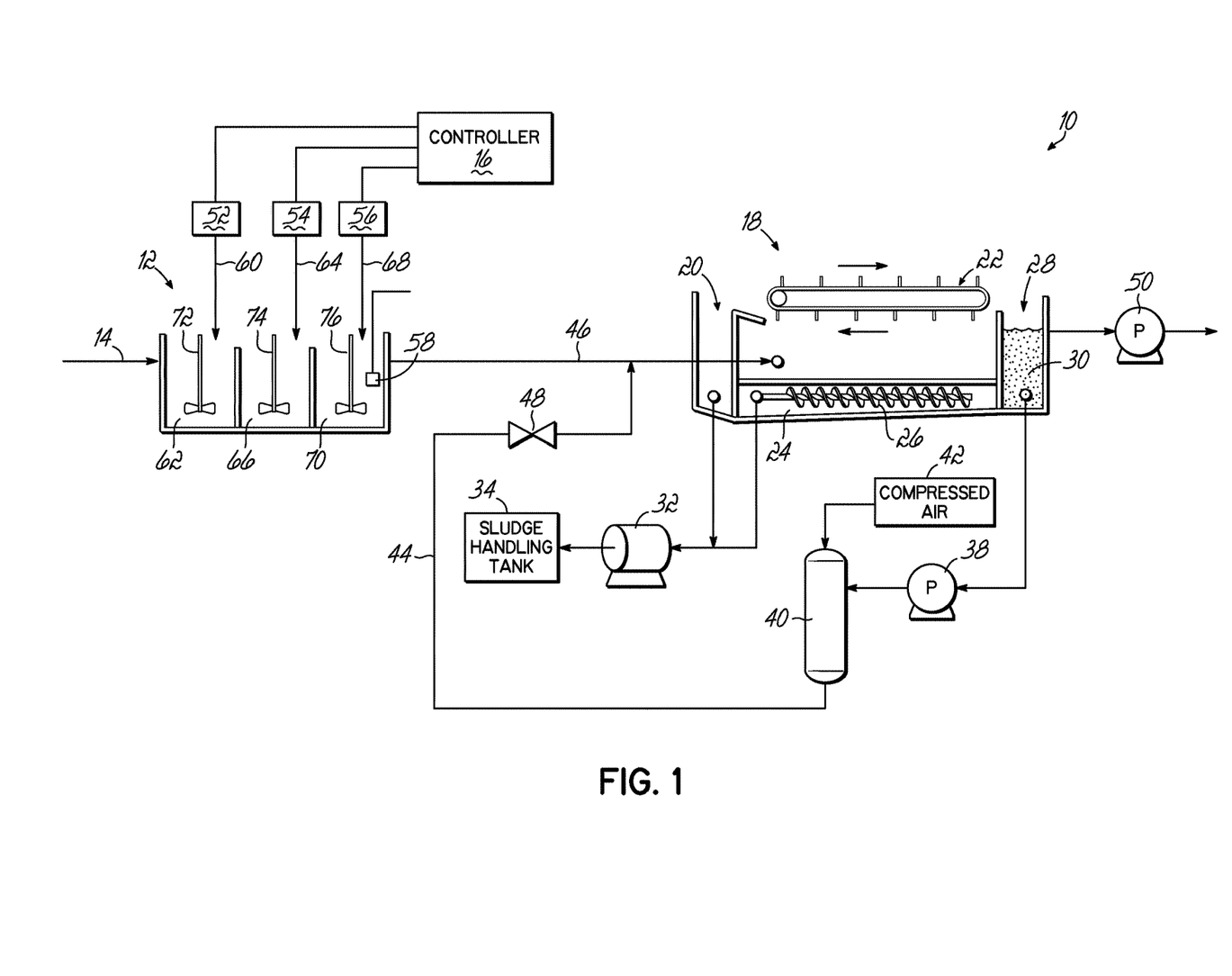
FIG. 1 is a schematic view of a wastewater treatment system that includes a reaction tank and a controller.

Referring now to FIG. 1, a wastewater treatment system 10 is illustrated that includes a primary reaction tank 12 which receives influent wastewater 14, a controller 16, and a Dissolved Air Floatation (DAF) unit 18. The DAF unit 18 includes a float storage chamber 20, a skimmer 22, a sediment discharge chamber 24 that collects heavy sediment and removes the sediment with an auger 26, and an effluent chamber 28 containing effluent 30. A sludge pump 32 coupled to the float storage chamber 20 and sediment discharge chamber 24 conveys solid waste that has floated to the top or settled to the bottom of the DAF unit 18 to one or more sludge handling tanks 34. To add dissolved air to the wastewater, a portion of the clarified effluent 30 may be removed from the effluent chamber 28 and conveyed by a recycle pump 38 to a pressure tank 40 where the portion of clarified effluent 30 is mixed with compressed air 42. To this end, the recycled effluent may be sprayed into the pressure tank 40 under several atmospheres of pressure. The small water droplets formed from the spray may thereby be saturated with pressurized air and collect in the bottom of the tank 40 to provide an aerated recycle stream 44.

The aerated recycle stream 44 may be introduced into the chemically treated wastewater 46 flowing out of the reaction tank 12 to provide dissolved air to the wastewater 46 prior to entering the DAF unit 18. As the aerated recycle stream 44 is introduced into the chemically treated wastewater 46, the air may come out of solution forming very small air bubbles that attach to floc particles in the chemically treated wastewater 46. A valve 48 may be used to control the amount of aerated recycle stream 44 introduced into the chemically treated wastewater 46, and to maintain the pressure in pressure tank 40 by restricting the flow of aerated recycle stream 44 out of the pressure tank 40. Effluent 30 that is to be discharged from the system 10 may be removed from the effluent chamber 28 by a discharge pump 50.

The controller 16 may be coupled to one or more chemical dispensers 52, 54, 56 that selectively dispense chemicals into the reaction tank 12 in response to signals from the controller 16. In an embodiment of the invention, one chemical dispenser 52 may dispense a coagulant 60 into a coagulation chamber 62 of reaction tank 12. Suitable coagulants may include inorganic coagulants, such as iron or aluminum salts, including ferric sulfate or aluminum chlorohydrate to name but a few. Suitable coagulants may also include combination inorganic/organic coagulants, such as Ashland ChargePac™ 55, ChargePac™ 60. ChargePac™ 7, ChargePac™ 10, or ChargePac™ 47, which are available from Ashland Inc. of Covington, Ky., United States. Similarly, another chemical dispenser 54 may dispense an acid or caustic solution 64 to a pH adjustment chamber 66 of the reaction tank 12 to adjust the pH of the wastewater. The pH of the wastewater may thereby be maintained at a level that optimizes the effectiveness of the coagulant. Finally, the additional chemical dispenser 56 may dispense a flocculant 68 to a flocculation chamber 70 of reaction tank 12. Suitable flocculants may include anionic flocculants, such as Ashland DF2205, DF2220, DF2270, and/or cationic flocculants such as Ashland DF2405. DF2428. DF2445, which are also available from Ashland Inc.

Each chamber 62, 66, 70 of reaction tank 12 may include a stirrer 72, 74, 76 to ensure that the added chemicals are evenly distributed throughout the wastewater. The operation of the stirrers may be adjusted to optimize the reactions in that portion of the primary reaction tank. For example, the stirrer 72 for the coagulation chamber 62 may operate at a higher speed than the stirrer 76 for the flocculation chamber 70 to optimize floc formation.

Figure 2:
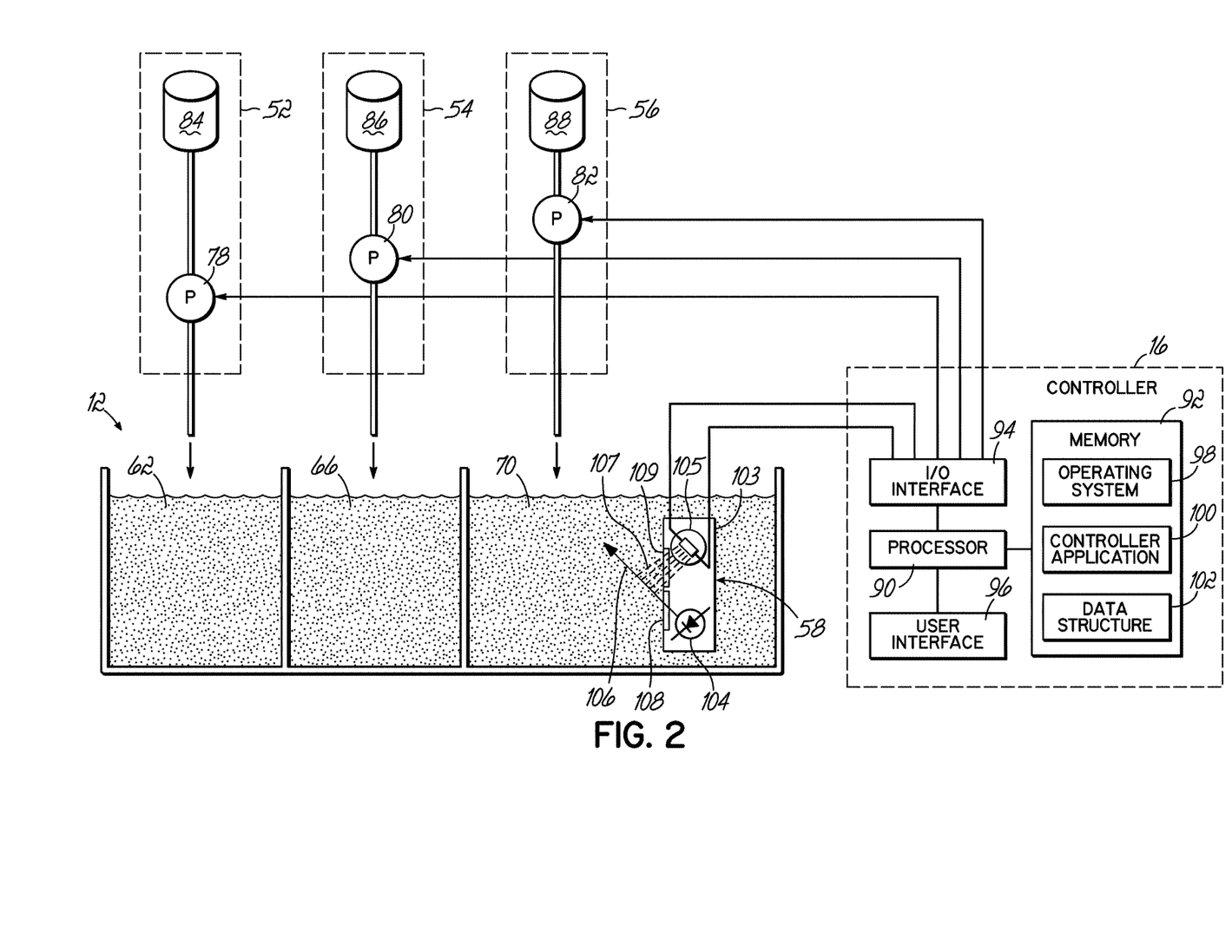
FIG. 2 is a schematic view of a portion of the wastewater treatment system of FIG. 1 showing additional details of the reaction tank and the controller.

Referring now to FIG. 2, a schematic view is presented that illustrates additional details of the controller 16, chemical dispensers 52, 54, 56, and turbidity sensor 58. Each chemical dispenser 52, 54, 56 may include a chemical dispensing pump 78, 80, 82 coupled to a respective container of chemical 84, 86, 88. Each chemical dispensing pump 78, 80, 82 is configured to dispense a controlled amount of the chemical from its respective chemical container 84, 86, 88 into the respective chamber 62, 66, 70 of reaction tank 12 in response to signals from the controller 16. In an alternative embodiment of the invention, the respective chemicals may be gravity fed into the reaction tank 12, in which case the pumps 78, 80, 82 may be replaced by valves (not shown) that are actuated by signals from the controller 16.

The controller 16 may be a commercially available controller, such as an OnGuardiController™, available from Ashland Inc., or any other device suitable for controlling the chemical dispensers 52, 54, 56 and monitoring the turbidity sensor 58. The controller 16 includes a processor 90, a memory 92, an input/output (I/O) interface 94, and a user interface 96. The processor 90 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 92. Memory 92 may be a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or any other device capable of storing digital information. Memory 92 may also include a mass storage device (not shown), such as a hard drive, optical drive, tape drive, non-volatile solid state device or any other device capable of storing digital information.

Processor 90 may operate under the control of an operating system 98 that resides in memory 92. The operating system 98 may manage controller resources so that computer program code embodied as one or more computer software applications, such as a controller application 100 residing in memory 92, may have instructions executed by the processor 90. In an alternative embodiment, the processor 90 may execute the applications 100 directly, in which case the operating system 98 may be omitted. One or more data structures 102 may also reside in memory 92, and may be used by the processor 90, operating system 98, and/or controller application 100 to store data.

The I/O interface 94 operatively couples the processor 90 to other components of the treatment system 10, such as the turbidity sensor 58, the coagulant dispensing pump 78, the caustic dispensing pump 80, and the flocculant dispensing pump 82. The I/O interface 94 may include signal processing circuits that condition incoming and outgoing signals so that the signals are compatible with both the processor 90 and the components to which the processor 90 is coupled. To this end, the I/O interface 94 may include analog-to-digital (A/D) and/or digital-to-analog (D/A) converters, voltage level and/or frequency shifting circuits, optical isolation and/or driver circuits, and/or any other analog or digital circuitry suitable for coupling the processor 90 to the other components of the treatment system 10.

The user interface 96 may be operatively coupled to the processor 90 of controller 16 in a known manner to allow a system operator to interact with the controller 16. The user interface 96 may include a display, such as a video monitor, alphanumeric displays, a touch screen, a speaker, and any other suitable audio and visual indicators capable of providing information to the system operator. User interface 96 may also include input devices and controls, such as an alphanumeric keyboard, a pointing device, keypads, push-buttons, control knobs, microphones, etc., capable of accepting commands or input from the operator and transmitting the entered input to the processor 90. In this way, user interface 96 may enable manual initiation or selection of system functions, for example, during system set-up, calibration, and chemical loading.

In the illustrated embodiment, the turbidity sensor 58 is a 90 degree scattered light sensor located in the flocculation chamber 70 of reaction tank 12. An example of a suitable 90 degree scattered light sensor is the Chemitec S461/T turbidity sensor from Liquid Analytical Resource, LLC of Shirley, Mass. United States. The turbidity sensor 58 may be located in the flocculation chamber 70, and may include a housing 103 containing a light source 104 and a light sensor 105. The light source 104 may include a laser diode, or other suitable light generating device that transmits a beam of light 106 into the wastewater. Portions of the beam of light 106 may be reflected and/or scattered by large and small solids contained within the wastewater of the flocculation chamber 70. Some of this scattered light 107 may be detected and measured by the light sensor 105, which may be configured to detect light scattered at an angle (e.g., a 90 degree angle) from the beam of light 106. Typically, the wastewater will be multiphase wastewater that contains liquid phase bulk water and solid phase floc particles. The wastewater may also contain gas phase bubbles. As the beam of light 106 passes through the wastewater, light from the beam of light 106 may be reflected off or scattered by particles in the wastewater, with a portion of this scattered light 107 being received by the light sensor 105.

Figure 3A:
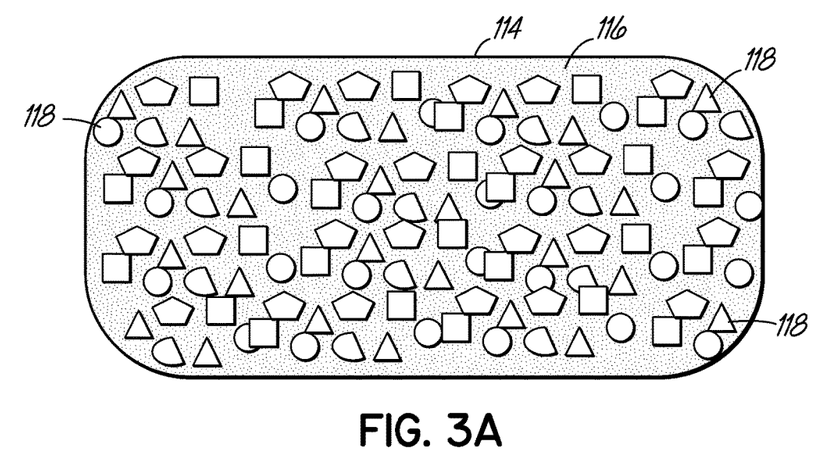
FIG. 3A is a diagrammatic view of a multiphase wastewater sample having a first level of turbidity.
Figure 3B:
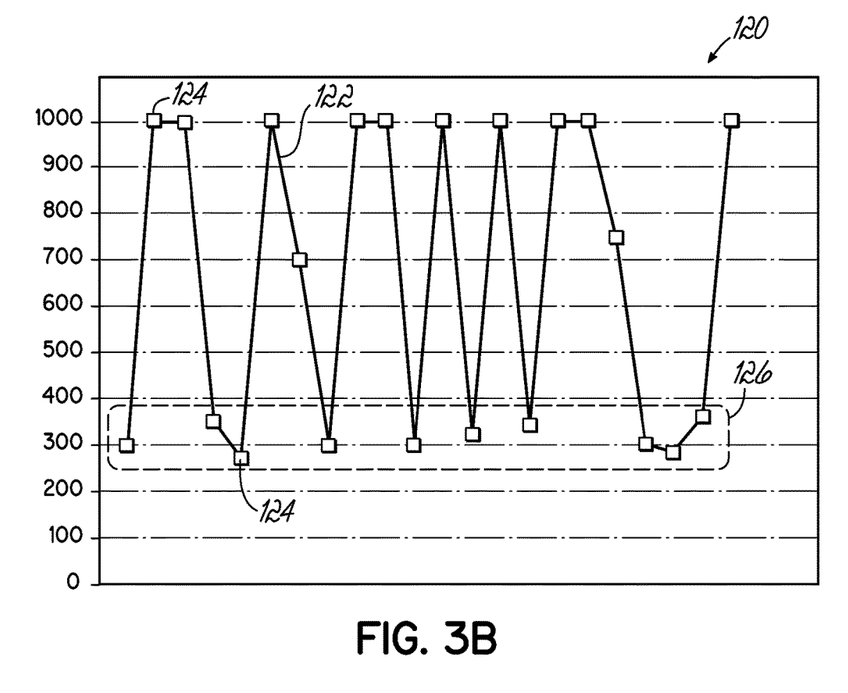
FIG. 3B is a graph showing samples of an output of a turbidity sensor corresponding to the sample in FIG. 3A.

To this end, the housing 103 may include one or more windows 108, 109 to prevent wastewater from entering the turbidity sensor 58. The windows 108, 109 may also enable the beam of light 106 to exit the housing 103 and the scattered light 107 to reach the light sensor 105. In response to receiving the scattered light 107, the light sensor 105 may generate an output signal 122 (FIG. 3), which may be a voltage or current that is proportional to the amount of scattered light 107 incident on the light sensor 105. This output signal 122 may, in turn, be coupled to the processor 90 via the I/O interface 94 of controller 16.

Although shown as located in the flocculation chamber 70, persons having ordinary skill in the art will understand that the light sensor 105 may be located in other areas of the treatment system 10 to measure turbidity in wastewater containing floc particles. For example, the turbidity sensor 58 may be located in the coagulation or pH adjustment chambers 62, 66, or between the flocculation chamber 70 and DAF unit 18. A person having ordinary skill in the art would also understand that a transmitted light sensor could be used in place of the scattered light sensor depicted. In embodiments using a transmitted light sensor, the light sensor 105 may be placed in the path of the beam of light 106. The signal provided by the light sensor 105 would thereby be reduced by the presence of floc and/or turbid water, rather than increased, due to the light being scattered. Thus, the signal provided by a transmitted light sensor would have an inverse relationship to the amount of turbidity and/or floc as compared to the signal provided by a scattered light sensor.

Figure 4A:
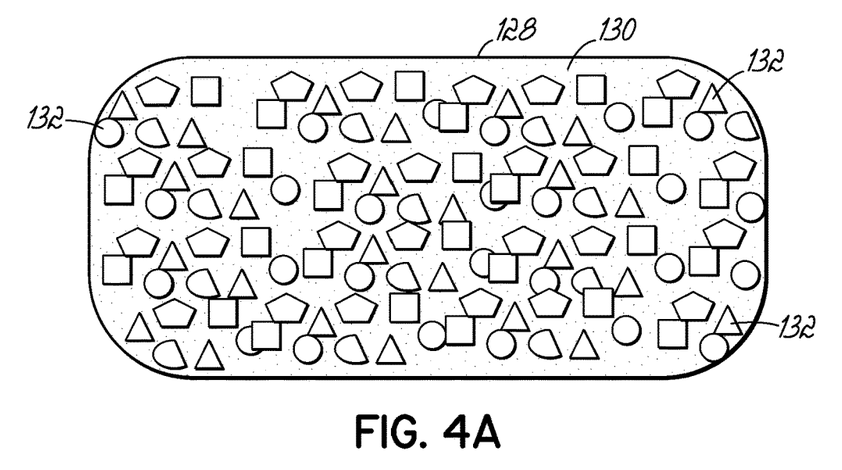
FIG. 4A is a diagrammatic view of a multiphase wastewater sample having a second level of turbidity lower than the first level of turbidity.
Figure 4B:
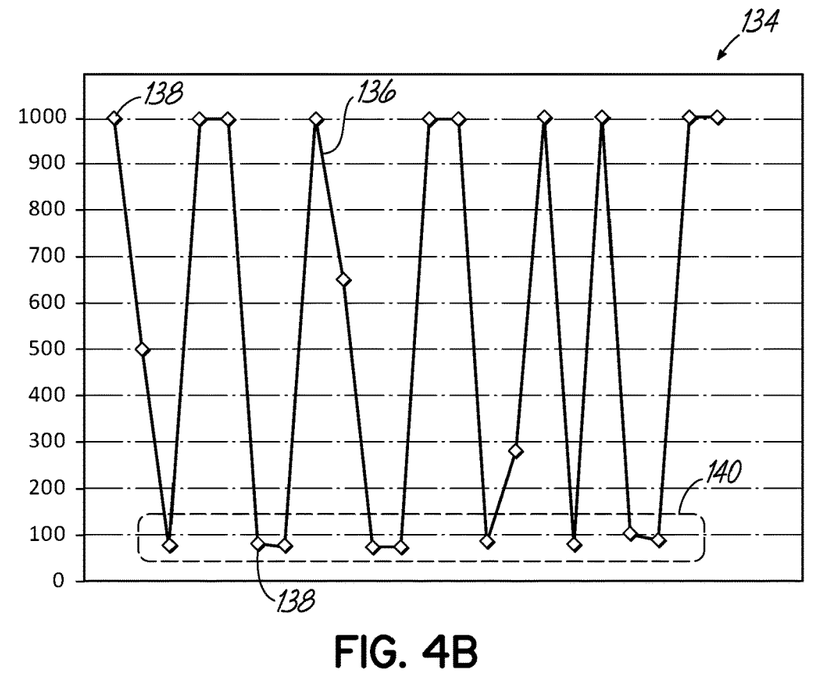
FIG. 4B is a graph showing samples of the output of the turbidity sensor corresponding to the sample in FIG. 4A.

Referring now to FIGS. 3A-4B, FIGS. 3A and 4A are diagrammatic views illustrating exemplary wastewater samples 114, 128 from the flocculation chamber 70 that include bulk water 116, 130 and floc particles 118, 132. FIGS. 3B and 4B provide graphs 120, 134 corresponding to respective samples 114, 128 that include plots of detected turbidity 122, 136 based on the output signal of the turbidity sensor 58 at a plurality of sample points 124, 138. In the exemplary graphs 120, 134, turbidity is indicated in Nephelometric Turbidity Units (NTU), although any suitable unit for measuring turbidity, or even a voltage or current level could also be used.

As wastewater from the flocculation chamber 70 is mixed and circulated, the beam of light 106 may at times only encounter bulk water 116, 130 as the beam of light 106 passes through the measuring distance of the turbidity sensor 58. During these times, samples 124, 138 of the turbidity detector output signal may group or cluster within a range of values that reflects the turbidity of the bulk water 116, 130. For example, in FIGS. 3A and 3B, the bulk water contains a relatively high level of turbidity represented by a portion of the samples 124 enclosed by the dotted line, so that a subset 126 of the samples 124 cluster within a range of 250 to 350 NTU. That is, the subset 126 of samples 124 falls within 50 NTU of a center value of 300 NTU. In contrast, FIGS. 4A and 4B show a sample having bulk water 130 with a lower turbidity, so that a portion, or subset 140 of the samples 138 fall within a range of 80 to 120 NTU, or within 20 NTU of a center value of 100 NTU. In each case, the subset of samples 126, 140 falls within a range that is correlated with the turbidity of the wastewater.

At other times, one or more floc particles 118, 132 and/or air bubbles may pass through the beam of light 106. At these times, the light reflected by the floc particles 118, 132 may cause the amount of light incident on the light sensor 105 to increase, so that the light sensor 105 generates a much higher output signal 122, 136. Accordingly, samples 124, 138 of the turbidity detector output signal taken at these times will typically fall well outside the range of values associated with bulk water subsets 126, 140. Moreover, these samples may fall within a range having a center value (e.g., 1000 NTU) that is significantly higher than the center value associated with the bulk water turbidity. The range of values for the samples 124, 138 associated with floc may be relatively independent of bulk water turbidity, so that there is little correlation between the sample values 124, 138 taken while a floc particle 118, 132 is reflecting the beam of light 106, and the turbidity of the wastewater. Therefore, this data may be identified and discarded so that only samples which were not affected by floc particles are relied upon to indicate turbidity. The amount of light reflected by the floc particles 118, 132 may be sufficient to cause the light sensor 105 to indicate a maximum turbidity or saturated output signal level, which in the exemplary embodiment, is shown as reading of 1000 NTU. However, persons having ordinary skill in the art will understand that this level may vary depending on the type of sensor used, as well as the characteristics of the floc. Embodiments of the invention are therefore not limited to any particular range of sample values being associated with detection of a floc particle.

It has been determined that by taking a plurality of samples and calculating a probability distribution of the indicated turbidity, accurate measurements of bulk water turbidity may be obtained in water samples containing floc. Advantageously, this allows determining the turbidity of wastewater in the flocculation chamber 70 in real time or near real time. By allowing the turbidity sensor 58 to be placed in the flocculation chamber 70 rather than at some point after the DAF unit 18, or other suitable floc removal device, such as a sedimentation clarifier (i.e., after the floc has been removed from the wastewater), embodiments of the invention may allow the controller 16 to react much more quickly to changes in wastewater turbidity than controllers in conventional systems. This quicker response time may, in turn, improve the accuracy with which coagulant levels are controlled, reducing the amount of wasted chemicals, as well as contamination levels in the effluent 30.

Figure 5:
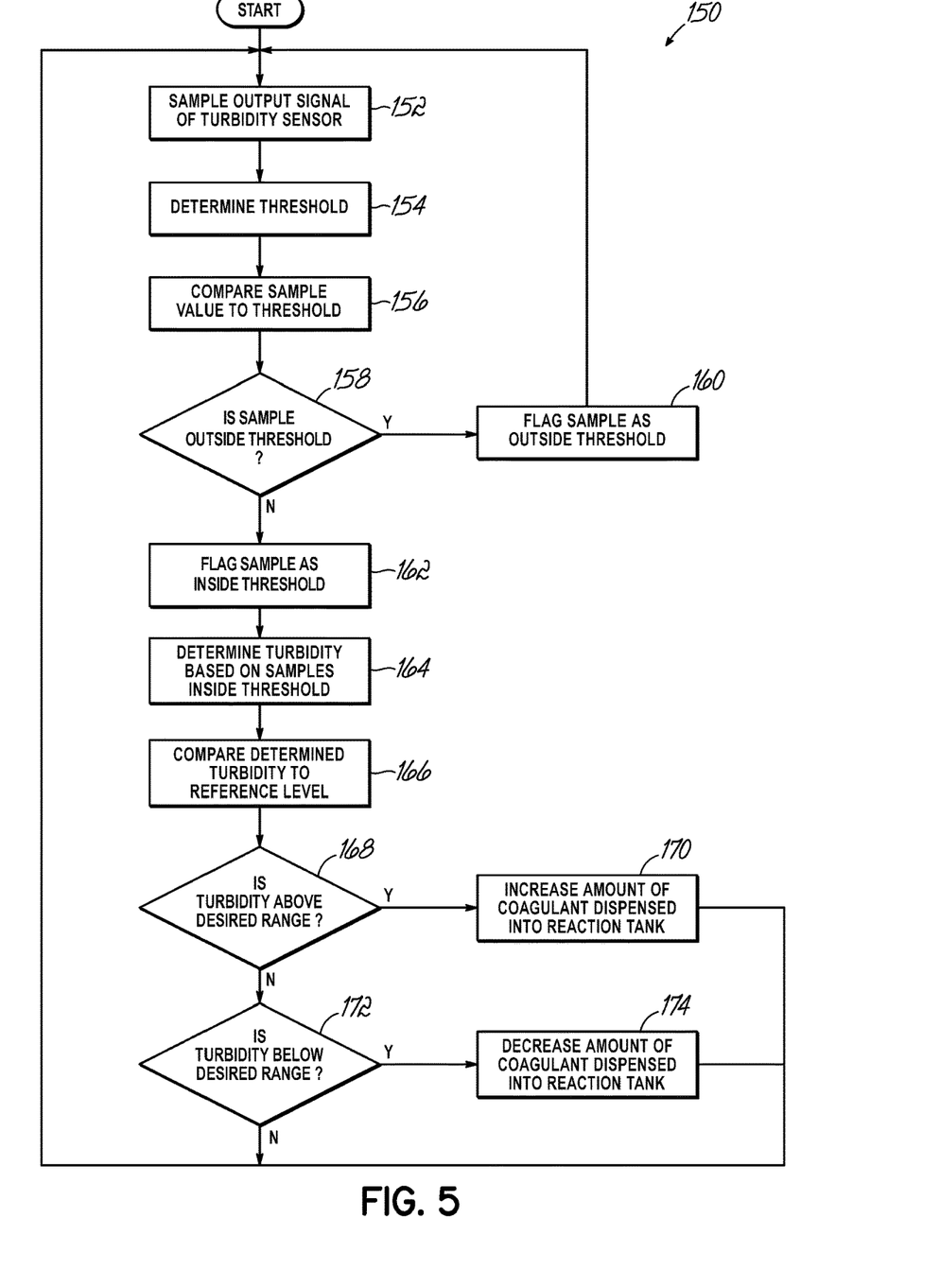
FIG. 5 is a flowchart of a process for sampling the output of the turbidity sensor and controlling dispensing of coagulant into the reaction tank of FIG. 2.

Referring now to FIG. 5, a flowchart 150 is presented in accordance with an embodiment of the invention that illustrates a sequence of operations for the controller application 100 that may be used to determine the turbidity of wastewater in the flocculation chamber 70. In block 152, the controller application 100 samples the output signal of the turbidity sensor 58. This sample may be assigned a value corresponding to the turbidity level indicated by the output signal of turbidity sensor 58, and may be stored as a data structure 102 in memory 92.

In block 154, the application 100 determines a threshold that may be used to classify the sample. Determining the threshold may include selecting a value from a look-up table based on the values of one or more output signal samples stored in memory 92, or may include a statistical analysis of a plurality of samples from a group of previously obtained samples. In an alternative embodiment of the invention, the threshold may be set to a predetermined value based on empirical data or an expected turbidity level in the flocculation chamber 70, in which case block 154 may be omitted. In any case, the threshold may include one or more values that separate the samples into a plurality of sample sets or clusters. For example, the threshold may have a lower value and a higher value that defines a signal range indicative of a bulk water reading, or the threshold may be a single value that represents signal value below which the reading is considered to be a bulk water reading.

In block 156, the application 100 compares the output signal sample obtained in block 152 with the threshold determined in block 154 before proceeding to decision block 158. If the output signal sample is outside the threshold (e.g. higher than the threshold) ("Yes" branch of decision block 158), the application flags the sample as outside the threshold in block 160 before returning to block 152 to take another sample. If the sample is inside the threshold (e.g. lower than or equal to the threshold) ("No" branch of decision block 158), the application 100 proceeds to block 162 and flags the sample as being inside the threshold. Samples flagged as outside the threshold may be discarded, or may be saved in memory 92 for use in determining future threshold levels. Samples flagged as being inside the threshold may be added to a set or subset of samples that are indicative of wastewater turbidity.

In block 164, the application 100 determines the turbidity of the wastewater based on the subset of samples that are flagged as being inside the threshold. Wastewater turbidity may be determined based on a statistical value of the samples. This statistical value may be an average or mean value of samples within the threshold, a median value of the samples within the threshold, a filtered value of the samples within the threshold (e.g., based on the output of a Finite Impulse Response (FIR) or Infinite Impulse Response (IIR) filter, or simply based on the last sample obtained that was flagged as being within the threshold. The subset of samples flagged as within the threshold may include a fixed number of samples selected based on a First In-First Out (FIFO) methodology, a number of samples obtained within a predetermined time window, or any other suitable method of defining the subset.

In block 166, the application 100 compares the determined turbidity to a reference level or value, which may represent a target turbidity level for the wastewater flowing out of the flocculation chamber 70. The difference between the determined turbidity level and the reference value may provide an error signal to a control algorithm in the controller application 100. For example, the error signal may be processed through a Proportional-Integral-Derivative (PID) control algorithm that produces an output indicating how much of a chemical, such as the coagulant, to add to the reaction tank 12. In an embodiment of the invention, the reference value may comprise an acceptable turbidity range. Turbidity values falling within this range would not produce an error signal, thereby producing a deadband or neutral zone in the controller output.

To this end, in decision block 168, if the determined turbidity is above the desired range or reference value ("Yes" branch of decision block 168), the controller application 100 may proceed to block 170. In block 170, the amount of coagulant added to the reaction tank 12 is increased. This increase may, for example, be accomplished by signaling the dispensing pump 78 to provide an increased amount of coagulant 60 to the coagulation chamber 62. If the determined turbidity is not above the desired range ("No" branch of decision block 168), the application 100 proceeds to decision block 172.

If the determined turbidity is below the desired range or reference value ("Yes" branch of decision block 172), the application 100 may proceed to block 174. In block 174, the application 100 decreases the amount of coagulant dispensed to the reaction tank 12. For example, the application 100 may signal the dispensing pump 78 coupled to the coagulant container 84 to reduce the flow rate of coagulant 60 provided to the coagulation chamber 62, or shut off the flow of coagulant 60 altogether. If the determined turbidity is not below the desired range ("No" branch of decision block 172), the application 100 may return to block 152 and obtain another sample of the turbidity sensor output signal.

The controller application 100 may thereby be configured to determine the turbidity of the bulk water 116, 130, and selectively activate one or more of the dispensing pumps 78, 80, 82 in response to signals from the turbidity sensor 58 so that the amounts of chemicals added to the influent wastewater are optimized. In an embodiment of the invention, the turbidity determination may also include determining a sample probability density based on the samples of the turbidity sensor output signal. This probability density function may be thought of as an expected distribution for a large population of samples, with a group of samples obtained by the controller application 100 serving as a random sample of that expected population.

Figure 6:
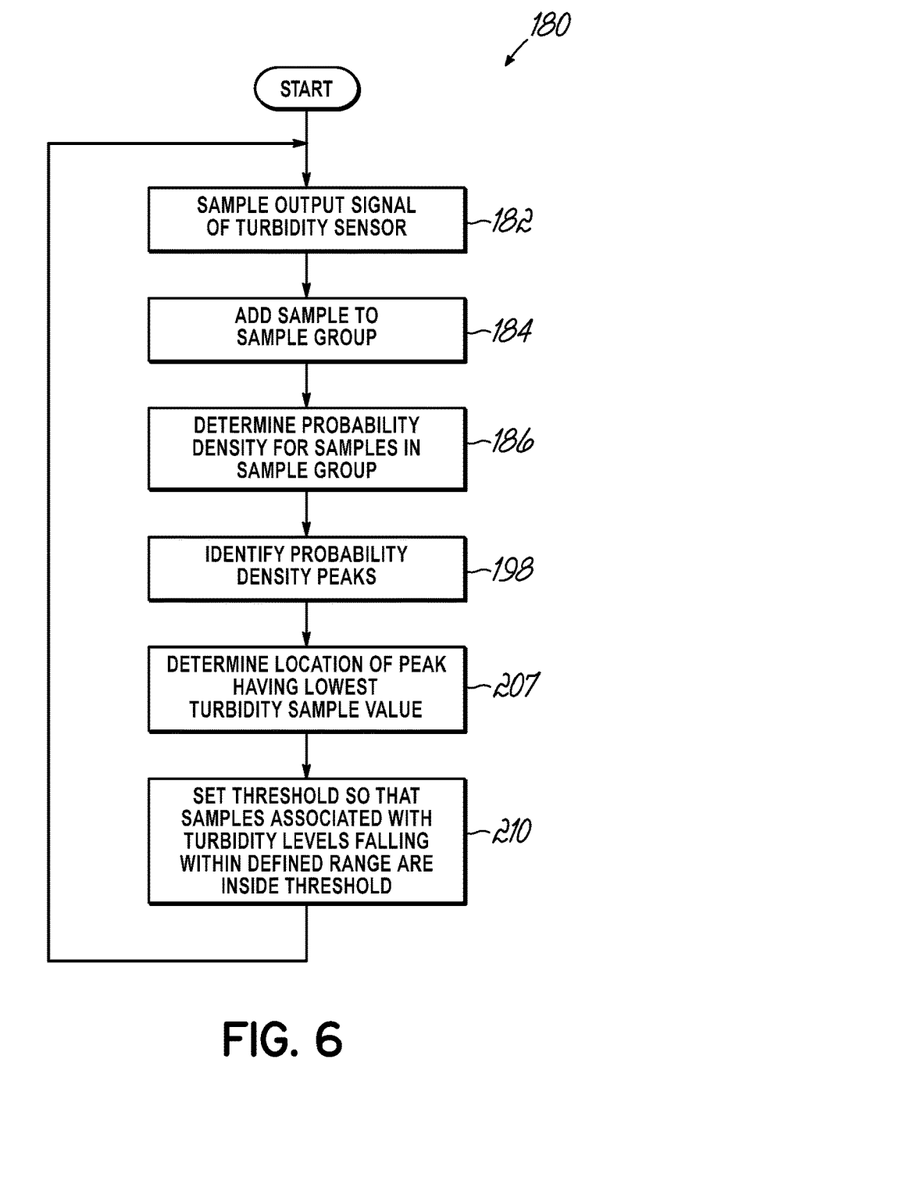
FIG. 6 is a flowchart of a process for analyzing the samples obtained in FIG. 5 to determine a signal threshold.

Referring now to FIG. 6, a flowchart 180 is presented in accordance with an embodiment of the invention. Flowchart 180 illustrates a sequence of operations that may be used to determine a threshold used to classify or identify turbidity sensor output signal samples that are indicative of wastewater turbidity. In block 182, the application 100 samples the output of the turbidity sensor 58. In block 184, this sample is added to a sample group. The sample group may represent a set of samples having a fixed number of samples, a set of samples collected over a moving window of time ending with the last sample, or any other suitable methodology for grouping samples.

Figure 7:
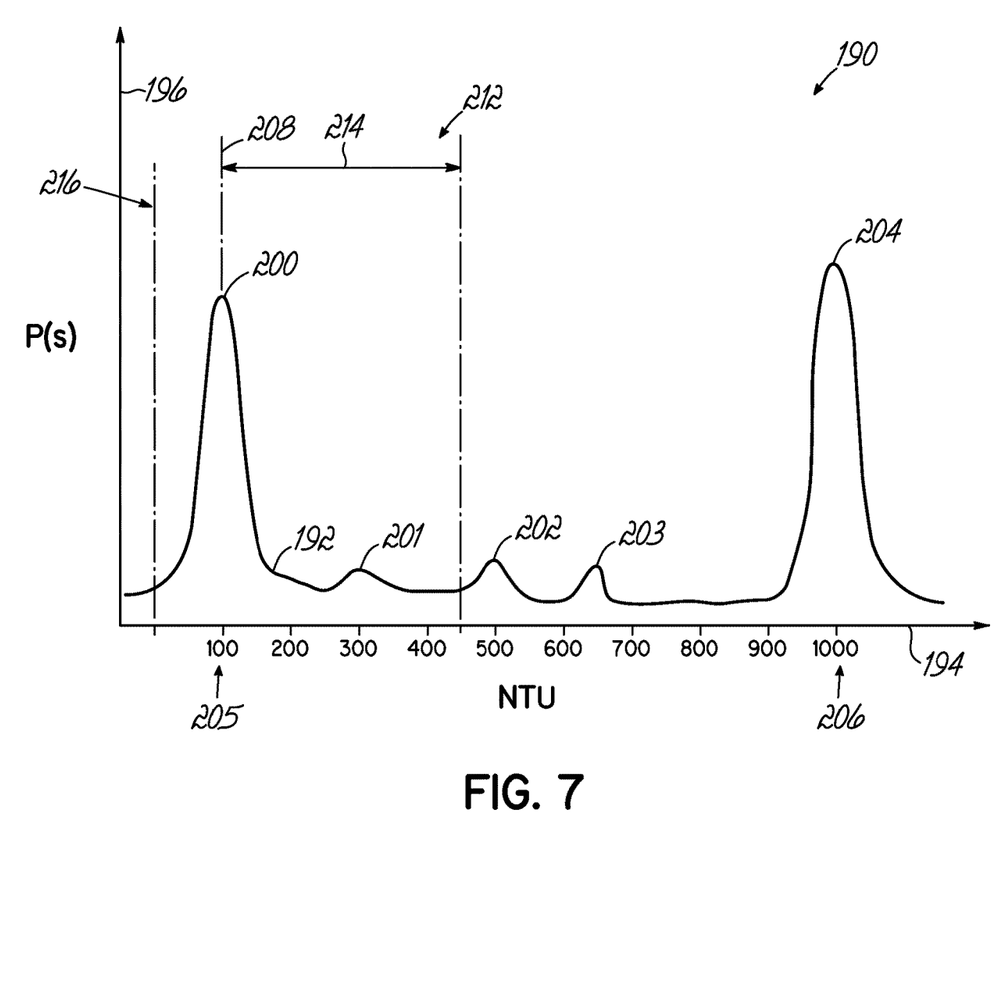
FIG. 7 is a graph showing a probability distribution for the samples illustrated in FIG. 4.

In block 186, the application 100 determines a probability density based on the sample group. To this end, the samples in the sample group may be viewed as a random sample from a larger universe of samples representing an expected output of the turbidity sensor 58. To illustrate this further, FIG. 7 presents an exemplary graph 190 of a probability density function represented by plot line 192 for the samples 138 shown in FIG. 4B. In the illustrated embodiment, the graph 190 has a horizontal axis 194 that provides the indicated turbidity level in NTU, and a vertical axis 196 that indicates the probability that a sample having that value of turbidity will be obtained. The controller application 100 may use any suitable method for determining the probability density function 192, such as a Parzen window, a data clustering technique, such as vector quantization, or by generating a rescaled histogram from the samples in the sample group. Once the probability density function 192 has been determined for the samples in the sample group, the controller application 100 may proceed to block 198.

In block 198, the controller application 100 may identify one or more peaks 200-204 of the probability density function 192. Although each of the one or more peaks 200-204 are shown as having a well defined maximum value in the exemplary graph 190, in embodiments of the invention, one or more of the peaks 200-204 may be flattened peaks, or may have a shape that lacks a well defined maximum value. For example, if a large number of samples 124, 138 are clustered near 300 NTU, there may be samples 124, 138 having other values (e.g. 1000, 5000, or 10,000 NTU) that do not form a readily identifiable peak. In any case, the peaks 200-204 may represent values of indicated turbidity that are more likely to be indicated by the output of the turbidity sensor 58. These expected turbidity sensor output levels may be concentrated in two peaks 200, 204, with one peak 200 located at a lower horizontal axis value 205 associated with wastewater turbidity readings (i.e., bulk water readings in the absence of floc scattering), and the other peak 204 located at a higher horizontal axis value 206 associated with an erroneous reading resulting from floc in the wastewater.

In block 207, the application 100 may identify the peak 200 occurring at the lowest horizontal axis value 205 (e.g., the lowest indicated NTU level) having a peak location 208. The application 100 may then proceed to block 210 and set a threshold 212 based on the location 208 of the identified peak 200. This threshold 212 may, for example, be set to a value that provides a desired distance 214 from the peak location 208. This distance 214 may, for example, be a predetermined distance (e.g., 100 NTU) or set to a predetermined number of standard deviations (e.g., $2 \times \sigma$) calculated for the sample group. The application 100 may also set a lower threshold 216 that sets a lower boundary for samples to be included in the sample group. That is, the application may define a range with thresholds 212, 216 that identifies samples to be included in the sample group.

It will be understood that when an element is described as being "connected" or "coupled" to or with another element, it can be directly connected or coupled to the other element or, instead, one or more intervening elements may be present. In contrast, when an element is described as being "directly connected" or "directly coupled" to another element, there are no intervening elements present. When an element is described as being "indirectly connected" or "indirectly coupled" to another element, there is at least one intervening element present.

As used herein, the term "in response to" means "in reaction to" and/or "after" a first event. Thus, a second event occurring "in response to" a first event may occur immediately after the first event, or may include a time lag that occurs between the first event and the second event. In addition, the second event may be caused by the first event, or may merely occur after the first event without any causal connection.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, although the invention has been described with respect to a turbidity sensor 58 having a 90 degree configuration between the light source 104 and light sensor 105, persons having ordinary skill in the art will understand that other types of sensors could be used. For example, a sensor that detects attenuation of a light source, or that is located at an angle other than 90 degrees with respect to the light source. In these alternative embodiments, the output signal of the turbidity sensor may be inverted with respect to the 90 degree sensor described herein. That is, a higher signal level may be indicative of a lower level of turbidity. The invention in its broader aspects is therefore not limited to the specific details, representative apparatus and methods and illustrative examples shown and described. Accordingly, departures may be made from such details without departing from the scope or spirit of Applicant's general inventive concept.

What is claimed:

1. A method of determining liquid phase turbidity of a multiphase wastewater consisting of:
    placing a turbidity sensor consisting of a housing unit containing a light emitter and a light sensor, into the multiphase wastewater prior to any dissolved air flotation unit or clarifier;
    emitting a light signal and receiving the signal at the light sensor indicative of an amount of light scattered by or transmitted through the wastewater;
    sampling the signal to produce a plurality of signal sample values wherein the sample values produced by the liquid phase of the wastewater in an absence of floc particles produces a first set of sample values and wherein the sample values produced when floc particles are in a path of the signal produces a second set of values;
    comparing the sample values to a threshold; wherein the threshold is based on a probability density distribution produced from the set of sample values produced from light scattered by the liquid phase without additional scattering or reflection from the floc particles; and
    setting the threshold so that at least a portion of the sample values lies below the threshold;
    identifying the sample values falling below the threshold; and
    determining the turbidity of the liquid phase of the wastewater based on the identified sample values.

2. The method of claim 1 further comprising:
    determining the threshold based at least in part on the values of the samples.

3. The method of claim 1 wherein determining the threshold further comprises:
    identifying the second group of samples having values clustered around the second signal value; and
    setting the threshold to a value between the first signal value and the second signal value.

4. The method of claim 3 wherein the second signal value is a value indicating a higher level of turbidity than the first signal value.

5. The method of claim 1 further comprising:
    generating a control signal based on the determined turbidity of the wastewater.

6. The method of claim 5 wherein:
    determining the turbidity of the wastewater includes determining a statistical value of falling below the threshold; and
    comparing the statistical value to a reference value, and based on the difference between the statistical value and a reference value setting the value of the control signal;
    wherein the statistical value may be an average or mean value of samples below the threshold, a median value of the samples below the threshold, a filtered value of the samples below the threshold filter, or based on the last sample obtained that was flagged as being below the threshold.

7. The method of claim 5 further comprising adjusting an amount of a chemical added to the wastewater based on the control signal.

8. The method of claim 7 wherein the chemical includes a coagulant.

9. An apparatus for treating wastewater consisting of:
    a processor; and
    a memory-containing program code that, when executed by the processor, causes the apparatus to:
    receive a signal indicative of an amount of light scattered by the liquid phase of the wastewater or by floc particles;
    sample the signal to produce a plurality of signal sample values;
    compare the sample values to a threshold;
    identify the sample values falling below the threshold; and
    determine the turbidity of the wastewater based on the identified sample values;
    wherein the threshold is based on a probability density distribution produced from the set of sample values produced from light scattered by the liquid phase without additional scattering or reflection from the floc particles.

10. The apparatus of claim 9 wherein the program code is further configured to cause the apparatus to determine the threshold based on the values of the samples by:
    identifying a first group of samples having values clustered around a first signal value;
    setting the threshold so that at least a portion of the first group of samples lies below the threshold.

11. The apparatus of claim 10 wherein the program code is further configured to cause the apparatus to further determine the threshold by:
    identifying a second group of samples having values clustered around a second signal value; and
    setting the threshold to a value between the first signal value and the second signal value, wherein
    the second signal value is a value indicating a higher level of turbidity than the first signal value.

12. The apparatus of claim 9 wherein the program code is further configured to generate a control signal based on the determined turbidity of the liquid phase of a multiphase wastewater.

13. The apparatus of claim 12 wherein the program code is configured to generate the control signal by:
- determining a statistical value of the samples falling below the threshold; and comparing the statistical value to a reference value, wherein the reference value is determined on the current liquid phase turbidity or light transmittance data, and based on the difference between the statistical value and a reference value setting the value of the control signal;
- wherein the statistical value may be an average or mean value of samples below the threshold, a median value of the samples below the threshold, a filtered value of the samples below the threshold filter, or based on the last sample obtained that was flagged as being below the threshold.

14. The apparatus of claim 12 wherein the control signal is used to adjust an amount of a chemical added to the wastewater.

15. The apparatus of claim 9 further comprising:
a turbidity sensor configured to sample multiphase wastewater containing floc and generate the signal indicative of the amount of light scattered by the floc in the wastewater.

16. A method of controlling liquid phase turbidity of multiphase wastewater consisting of:
- transmitting a beam of light from a light source into the multiphase wastewater; detecting an amount of light scattered or transmitted through the wastewater at a light sensor, wherein the light sensor generates an output signal that is proportional to the amount of scattered or transmitted light incident to the light sensor;
- receiving the output signal at a processor, wherein the processor produces a plurality of signal sample values, wherein the sample values produced by the liquid phase of the wastewater in an absence of floc particles produces one set of sample values and wherein the sample values produced when floc particles are in a path of the signal produces a second set of values;
- comparing the signal sample values to a threshold; wherein the threshold is based on a probability density distribution produced from a first set of sample values produced from light scattered by the liquid phase without additional scattering or reflection from the floc particles;
- determining the turbidity of the liquid phase of the wastewater based on the identified sample values; and
- adding a chemical additive to the wastewater system to achieve a desired turbidity.

17. The method of claim 16, wherein the light sensor detects the amount of scattered light through the wastewater wherein the detected light is proportional to the amount of scattered light incident to the light sensor.

* * * * *